United States Patent
Yang et al.

(10) Patent No.: US 10,465,154 B2
(45) Date of Patent: Nov. 5, 2019

(54) SELF-LOCKING OPTOELECTRONIC TWEEZER AND ITS FABRICATION

(71) Applicant: The Regents of the University of California, Oakland, CA (US)

(72) Inventors: Yajia Yang, Los Angeles, CA (US); Yufei Mao, Los Angeles, CA (US); Pei-Yu E. Chiou, Los Angeles, CA (US); Chi On Chui, Encino, CA (US)

(73) Assignee: The Regents of the University of California, Oakland, CA (US)

( * ) Notice: Subject to any disclaimer, the term of this patent is extended or adjusted under 35 U.S.C. 154(b) by 267 days.

(21) Appl. No.: 15/501,428

(22) PCT Filed: Aug. 14, 2015

(86) PCT No.: PCT/US2015/045387
§ 371 (c)(1),
(2) Date: Feb. 2, 2017

(87) PCT Pub. No.: WO2016/025901
PCT Pub. Date: Feb. 18, 2016

(65) Prior Publication Data
US 2017/0226453 A1    Aug. 10, 2017

Related U.S. Application Data

(60) Provisional application No. 62/038,150, filed on Aug. 15, 2014, provisional application No. 62/181,627, filed on Jun. 18, 2015.

(51) Int. Cl.
*G01N 27/453* (2006.01)
*G01N 27/447* (2006.01)
(Continued)

(52) U.S. Cl.
CPC ......... *C12M 1/42* (2013.01); *B01L 3/502707* (2013.01); *B01L 3/502715* (2013.01); *B01L 3/502761* (2013.01); *B03C 5/005* (2013.01); *B03C 5/026* (2013.01); *G02B 21/32* (2013.01); *B01L 2200/0668* (2013.01); *B01L 2400/0454* (2013.01); *B03C 2201/26* (2013.01); *C12M 3/00* (2013.01); *G01N 15/10* (2013.01); *G01N 2035/1046* (2013.01)

(58) Field of Classification Search
CPC .......... B03C 5/005; B03C 5/026; B03C 5/028
See application file for complete search history.

(56) References Cited

U.S. PATENT DOCUMENTS 7,612,355 B2    11/2009  Wu et al.
7,956,339 B2     6/2011  Otha et al.
(Continued)

FOREIGN PATENT DOCUMENTS

WO    WO 2016/025901 A1    2/2016

OTHER PUBLICATIONS

Hsu et al., "Phototransistor-based optoelectronic tweezers for dynamic cell manipulation in cell culture media," Lab Chip, 2010, 10, 165-172 (Year: 2010).*
(Continued)

*Primary Examiner* — Alexander S Noguerola
(74) *Attorney, Agent, or Firm* — Tom Hunter; Weaver Austin Villeneuve & Sampson LLP

(57) ABSTRACT

A novel Self-Locking Optoelectronic Tweezers (SLOT) for single microparticle manipulation across a large area is provided. DEP forces generated from ring-shape lateral phototransistors are utilized for locking single microparticles or cells in the dark state. The locked microparticles or cells can be selectively released by optically deactivating these locking sites.

34 Claims, 17 Drawing Sheets

(51) Int. Cl.
*C12M 1/42* (2006.01)
*B01L 3/00* (2006.01)
*G02B 21/32* (2006.01)
*B03C 5/00* (2006.01)
*B03C 5/02* (2006.01)
*G01N 15/10* (2006.01)
*G01N 35/10* (2006.01)
*C12M 3/00* (2006.01)

(56) References Cited

U.S. PATENT DOCUMENTS

| | | | |
|---|---|---|---|
| 2008/0017808 | A1 | 1/2008 | Dholakia et al. |
| 2009/0170186 | A1 | 7/2009 | Wu et al. |
| 2009/0258383 | A1 | 10/2009 | Kovac et al. |
| 2010/0101960 | A1 | 4/2010 | Otha et al. |
| 2014/0124370 | A1 | 5/2014 | Short et al. |
| 2014/0216935 | A1 | 8/2014 | Vezenov |
| 2016/0318038 | A1 | 11/2016 | Short et al. |

OTHER PUBLICATIONS

Web article entitled "Basic Visible and Infrared Light Detectors", author unknown, downloaded Jan. 16, 2019 from http://www.circuitous.ca/PhotoDetectors.html, published Mar. 26, 2012 (Year: 2012).*

Web article by Forrest Mims, III, entitled "Amateur Scientist: Experimenting with Light and Dark Sensors", downloaded Jan. 16, 2019 from https://makezine.com/projects/make-38-cameras-and-av/light-and-dark-sensors/, published Apr. 24, 2014 (Year: 2014).*

"3.2 Comparing Prokaryotic and Eukaryotic Cells" downloaded Jan. 17, 2019 from https://bio.libretexts.org/Bookshelves/Introductory_and_General_Biology/Book%3A_Concepts_in_Biology_(OpenStax)/3%3A_Cell_Structure_and_Function/3.2%3A_Comparing_Prokaryotic_and_Eukaryotic_Cells (Year: 2017).*

Encylopedia Britanica article entitled "Embryo—Human and Animal" downloaded Jan. 16, 2019 from https://www.britannica.com/science/embryo-human-and-animal (Year: 2018).*

PCT International Search Report and Written Opinion dated Nov. 23, 2015 issued in PCT/US15/45387.

PCT International Preliminary Report on Patentability dated Feb. 21, 2017 issued in PCT/US15/45387.

EP Extended European Search Report dated Mar. 19, 2018 issued in EP15831613.3.

EP Office Action dated Dec. 14, 2018 issued in EP15831613.3.

Chiou et al. (2005) "Massively parallel manipulation of single cells and microparticles using optical images." *Nature* 436(7049): 370-372.

Huang et al. (2013) "Optoelectronic tweezers integrated with lensfree holographic microscopy for wide-field interactive cell and particle manipulation on a chip." *Lab Chip*, 13(12): 2278-2284.

* cited by examiner

Test of Self-locking effect

Micro-beads randomly distributed

Micro-beads in orderly manner

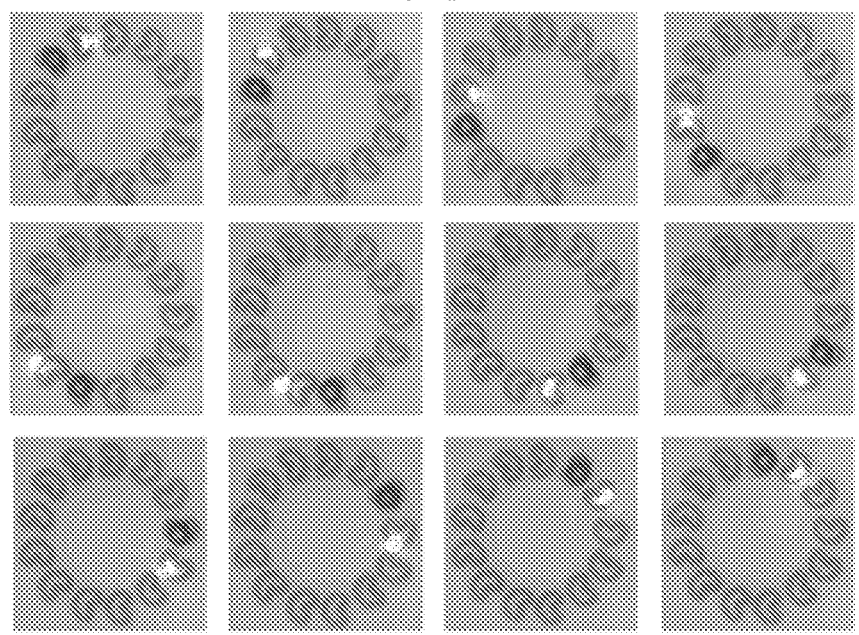
*Fig. 15, cont'd.*

SELF-LOCKING OPTOELECTRONIC TWEEZER AND ITS FABRICATION

CROSS-REFERENCE TO RELATED APPLICATIONS

This application is a U.S. 371 National Phase of PCT/US2015/045387, filed on Aug. 14, 2015, which claims benefit of and priority to U.S. Ser. No. 62/038,150, filed on Aug. 15, 2014, and to U.S. Ser. No. 62/181,627, filed on Jun. 18, 2015, all of which are incorporated herein by reference in their entirety for all purposes.

STATEMENT OF GOVERNMENT SUPPORT

The invention was made with government support under Grant No. 1232279 awarded by the National Science Foundation. The Government has certain rights in the invention.

BACKGROUND

Optoelectronic Tweezers (OET) has been developed for parallel manipulation of single cells and particles for a variety of biological applications (Chiou et al. (2005) *Nature* 436(7049): 370-372.). For example Optoelectronic Tweezers (OET) has been developed for dynamic manipulation of single cells and particles (Chiou et al. (2005) *Nature*, 436 (7049): 370-372). OET can be used for trapping and manipulation of semiconducting and metallic nanowires (Jamshidi et al. (2008) *Nature Photonics*, 2(2): 86-89), micro/nano beads (Ota et al. 92013) *Nano Letts.*, 13(6): 2766-2770; Glaesener et al, (2012) *Optics Letts.*, 37(18): 3744-3746; Zarowna-Dabmwska et al. (2011) *Optics Express*, 19(3): 2720-2728), DNA (Jamshidi et al. (2009) *Nano Letts.*, 9(8): 2921-2925), and biological cells (Jeorrett et al. (2014) *Optics Express* 22(2): 1372-1380; Shah et al. (2009) *Lab on a Chip*, 9(12): 1732-1739).

In a typical OET setting, large numbers (e.g., over 15,000) of individually addressable light traps can be formed across an area of 1 $mm^2$ in low conductivity media (~0.01 S/m). However, the utility of OET has been bottlenecked by its incompatibility with physiological buffers and low manipulation throughput. Previously, vertical phototransistor-based OET (Hsu et al. (2010) *Lab on a Chip*, 10(2): 165-172) has been proposed to address the buffer incompatibility issue. Low throughput, however, remains a major issue for all optical manipulation technologies, including, but not limited to OET. This fundamental limitation comes from the trade-off between field-of-view (FOV) and optical resolution. Large FOV, in general, means using lenses with low numerical aperture (N.A.). Such low numerical aperture lenses, however, cannot provide the required optical image sharpness to create a light intensity gradient that generates sufficient trapping forces. This is true for both direct optical forces in optical tweezers and light-induced DEP forces in OET. Consequently, large-area optical manipulation of single cells or particles is nearly impossible even with high-power light beam.

SUMMARY

Various embodiments contemplated herein may include, but need not be limited to, one or more of the following:

Embodiment 1: A self-locking optoelectronic tweezers device including: a first substrate including a first electrode and a plurality of annular and/or non-circular phototransistors that can be optically turned on and off, wherein said phototransistors and first substrate are configured to produce a negative dielectrophoretic (DEP) force at the annular or non-circular phototransistors on application of a voltage to said device; and that turn off the DEP at an annular or bean-shaped (e.g., kidney bean shaped) phototransistor when that phototransistor is illuminated with light; and a surface including a second electrode, wherein said surface is disposed to define a chamber or channel between said first substrate and said surface and said chamber or channel is configured to receive and, or to hold a fluid containing cells or particles.

Embodiment 2: The device of embodiment 1, wherein said phototransistors are annular.

Embodiment 3: The device of embodiment 1, wherein said non-circular phototransistors are bean-shaped (e.g., kidney-bean shaped).

Embodiment 4: The device of embodiments 1-3, wherein said phototransistors create an electric field perpendicular to the plane of the apparatus.

Embodiment 5: The device of embodiments 1-4, wherein the annular or non-circular portion of said phototransistors is p-doped.

Embodiment 6: The device of embodiments 1-5, wherein said substrate is a doped p-type substrate including annular or bean portions wherein the center of the annular or bean-shaped portions and the regions outside said annular or non-circular portions are n-doped.

Embodiment 7: The device of embodiment 6, wherein said doped p-type substrate is a doped p-type Group III-V or p-type group IV material.

Embodiment 8: The device of embodiment 6, wherein said doped p-type substrate is doped p-type silicon.

Embodiment 9: The device of embodiment 6, wherein said n-doped regions are coated with a thin film conductor.

Embodiment 10: The device of embodiment 9, wherein said thin film conductor one or more includes materials selected from the group consisting of Au, Ti, Al, Cr, Ni, Ta, Pd, and Pt.

Embodiment 11: The device of embodiment 1, wherein the annular or non-circular portion of said phototransistors are n-doped.

Embodiment 12: The device of embodiments 1, and 6, wherein said substrate is a doped n-type substrate including annular or non-circular portions wherein the center of the annular or non-circular portions and the regions outside said annular or non-circular portions are p-doped.

Embodiment 13: The device of embodiment 12, wherein said doped n-type substrate is a doped n-type Group III-V, or n-type group IV material.

Embodiment 14: The device of embodiment 12, wherein said doped n-type substrate is doped n-type silicon.

Embodiment 15: The device of embodiment 12, wherein said p-doped regions are coated with a thin film conductor.

Embodiment 16: The device of embodiment 15, wherein said thin film conductor one or more includes materials selected from the group consisting of Au, Ti, Al, Cr, Ni, Ta, Pd, and Pt.

Embodiment 17: The device of embodiments 1-15, wherein a top surface of said substrate is coated with an insulator with openings to the conductor film in the center of the annulus or non-circular shape.

Embodiment 18: The device of embodiment 17, wherein said insulator includes a material selected from the group consisting of SU-8 or other photoresists, PDMS, silicon dioxide, $Al_2O_3$, and silicon nitride.

Embodiment 19: The device of embodiments 17-18, wherein said insulation layer is configured to provide about a 50% partial voltage leak in the dark state.

Embodiment 20: The device of embodiments 17-19, wherein said insulator includes $Al_2O_3$.

Embodiment 21: The device of embodiment 20, wherein the thickness of $Al_2O_3$ layer including said insulator is about 30 nm.

Embodiment 22: The device of embodiments 1-21, wherein said substrate ranges in size from about 1 $mm^2$ or from about 5 $mm^2$, or from about 10 $mm^2$, or from about 50 $mm^2$, or from about 1 $cm^2$ up to about 500 $cm^2$, or up to about 200 $cm^2$ or up to about 100 $cm^2$ or up to about 50 $cm^2$.

Embodiment 23: The device of embodiments 1-22, wherein the diameter of an annulus or the major axis of a non-circular shape ranges from sub-micron size (e.g., for trapping molecules) to hundreds of micrometers to trap large objects (e.g., aggregations of cells).

Embodiment 24: The device of embodiments 1-23, wherein the diameter of an annulus or the major axis of a non-circular shape ranges from about 10, or from about 20 nm, or from about 50 nm, or from about 100 nm, or from about 200 nm, or from about 500 nm up to about 500 μm, or up to about 250 μm, or up to about 200 μm, or up to about 100 μm, or up to about 150 μm, or up to about 100 μm, or up to about 80 μm, or up to about 60 μm, or up to about 50 μm, or up to about 30 μm, or up to about 20 μm.

Embodiment 25: The device of embodiment 24, wherein the diameter of an annulus or the major axis of a non-circular shape is about 10 μm to about 20 μm.

Embodiment 26: The device of embodiment 24, wherein the diameter of an annulus or the major axis of a non-circular shape is about 15 μm.

Embodiment 27: The device of embodiments 1-26, wherein the thickness of the ring forming an annulus or non-circular shape ranges from about 0.5 μm up to about 10 μm.

Embodiment 28: The device of embodiments 1-26, wherein the thickness of the ring forming an annulus or non-circular shape ranges from about 2 μm up to about 8 μm.

Embodiment 29: The device of embodiments 1-26, wherein the thickness of the ring forming an annulus or non-circular shape is about 5 μm.

Embodiment 30: The device of embodiments 1-29, wherein said chamber or channel contains a physiological buffer.

Embodiment 31: The device of embodiments 1-29, wherein said chamber or channel contains an isotonic buffer.

Embodiment 32: The device of embodiments 1-31, wherein said chamber or channel contains particles.

Embodiment 33: The device of embodiments 1-31, wherein said chamber or channel contains cells.

Embodiment 34: The device of embodiments 1-31, wherein said chamber or channel contains prokaryotic cells.

Embodiment 35: The device of embodiment 34, wherein said chamber or channel contains bacterial cells Embodiment 36: The device of embodiments 1-31, wherein said chamber or channel contains eukaryotic cells.

Embodiment 37: The device of embodiment 36, wherein said chamber or channel contains insect cells, mammalian cells, or avian cells.

Embodiment 38: The device of embodiments 1-31, wherein said chamber or channel contains an egg or an embryo.

Embodiment 39: A method of trapping cells or particles, said method including: introducing cells or particles into a chamber of a device according to embodiments 1-28; and applying a voltage between said first electrode and said second electrode to said first electrode to trap said cells or particles at annular transistors including said substrate.

Embodiment 40: The method of embodiment 39, further including illuminating one or more phototransistors to release trapped particles or cells.

Embodiment 41: The method of embodiments 39-40, wherein said voltage is an AC voltage.

Embodiment 42: The method of embodiment 41, wherein said voltage ranges from about 0.5 V to about 100 V pp.

Embodiment 43: The method of embodiments 41-42, wherein the frequency of said voltage ranges from about 1 kHz to about 50 MHz.

Embodiment 44: The method of embodiments 39-43, wherein said chamber or channel contains a physiological buffer.

Embodiment 45: The method of embodiments 39-43, wherein said chamber or channel contains an isotonic buffer.

Embodiment 46: The method of embodiments 39-45, wherein said chamber or channel contains particles or particle clusters.

Embodiment 47: The method of embodiments 39-45, wherein said chamber or channel contains cells or cell clusters.

Embodiment 48: The method of embodiment 47, wherein said chamber or channel contains prokaryotic cells.

Embodiment 49: The method of embodiment 48, wherein said chamber or channel contains bacterial cells.

Embodiment 50: The method of embodiment 47, wherein said chamber or channel contains eukaryotic cells.

Embodiment 51: The device of embodiment 50, wherein said chamber or channel contains insect cells, mammalian cells, or avian cells.

Embodiment 52: The method of embodiments 39-45, wherein said chamber or channel contains an egg or an embryo.

BRIEF DESCRIPTION OF THE DRAWINGS

FIG. 4, panel (b) Voltage-on and Light-off. Two particles are self-locked. FIG. 4, panel (c) Voltage-on and Light-on. Particle 2 is kicked out of the trapping site. FIG. 4, panel (d) Voltage-on and Light-off. Particle 2 is removed while Particle 1 stays at the same location.

DETAILED DESCRIPTION

In various embodiments, a self-locking optoelectronic tweezers (SLOT) is provided. The Self-Locking Optoelectronic Tweezers (SLOT) platform described herein that overcomes the blur optical pattern issue for large area single cell and microparticle manipulation. The SLOT platform described herein provides convenient and effective manipulation of single cells or microparticles in physiological buffers or other buffers (e.g., such as isotonic buffers commonly used in DEP technologies) across large areas. The SLOT can be used, inter alia, in sorting rare cells or particles, for in vitro fertilization, in tissue engineering, and in various other contexts where manipulation of single cells or particles is desirable.

It is believed that all prior OET platforms require the projection of light beams to form DEP traps, either positive or negative. This means that cells and particles cannot be trapped without light beams present. To trap a cell using a light beam two criteria need to be satisfied. One the light intensity needs to be strong enough so that that it can create a virtual electrode and trigger enough electric field to trap cells. Second, a commonly ignored factor but critically important for large area single cell manipulation, is the sharpness of the projected light patterns. A blurred light pattern, even though strong enough to turn on virtual electrodes, cannot generate large enough DEP forces for cell manipulation since DEP force is linearly proportional to the gradient of the electric field strength. A blurry light pattern with a slow varying intensity profile does not generate a large enough electric field gradient resulting in DEP forces sufficient for effective trapping and manipulation of cells.

The sharpness (or the resolution) of the projected light pattern is determined by the numerical aperture (N.A.) of the optical system. To keep a good sharpness for effective OET manipulation, a 10× objective lens is typically used in most OET platforms. However, a 10× objective lens only has a field of view (FOV) of 1~2 $mm^2$. Increasing the manipulation area using a convex lens with a lower N.A. is possible, but this greatly sacrifices the manipulation force as we demonstrated in holographic OET, ~1 $cm^2$ (Hsu et al. (2010) *Lab chip*, 19(2): 165-172). As a result, it is believed to be almost impossible to further extend the single cell manipulation area on OET. The trade-off between high optical resolution pattern and large field-of-view manipulation is a fundamental physical barrier.

Self-Locking Optoelectronic Tweezers described herein provide a new optical manipulation approach and a platform that can bypass such fundamental barrier to provide high-resolution single cell manipulation functions using light beams over an extremely large area, potentially hundreds of $cm^2$ depending on wafer size, and electrical power that can be supplied.

Figure 1:
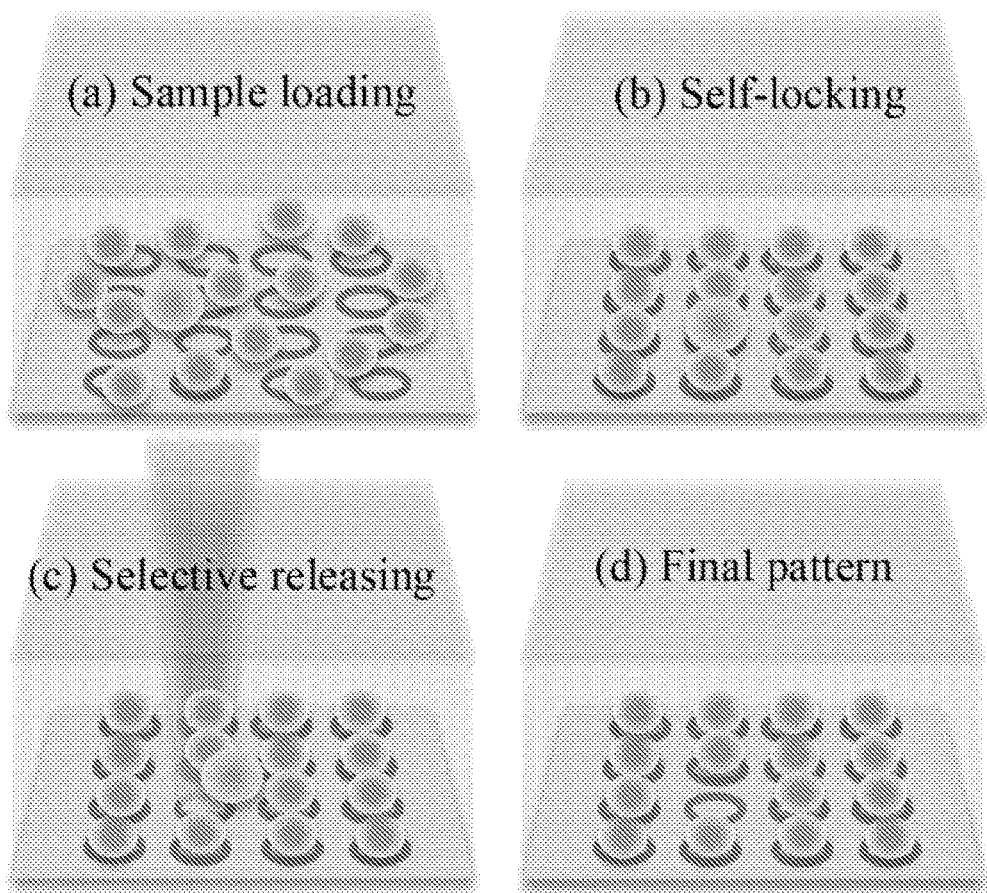
FIG. 1, panels A-D, schematically illustrates the operation of SLOT. (a) Sample loading. Microparticles are scattered over the device surface. (b) Self-locking. Once an AC voltage is applied, microparticles are locked to the center of ring-shape electrodes. (c) Selective releasing. A light beam is used for single particle releasing. (d) Final pattern. Single targeting particle is released.

In various embodiments, the SLOT system comprises one or more "top" electrodes, bottom phototransistors and fluid channels or chambers (e.g., microfluidic channels) in between. FIG. 1 schematically illustrates the operating principle of a SLOT platform. First, particles or cells are introduced into a channel or chamber between the top electrode and the phototransistor substrate (e.g. flowed in through a microfluidic channel) as shown in FIG. 1(*a*). The top and bottom electrodes are wired to an external voltage source (e.g., a function generator). Once an AC voltage is applied, dielectrophoretic (DEP) traps (negative traps and particles are locked in weak electric field regions) will form and lock individual particles or cells (or clusters of particles or cells) to their neighboring ring (annular) phototransistors as shown in FIG. 1(*b*). Optical observation (e.g., fluorescence, dark field, phase contrast, and others) can be performed to identify particles or cells of interest. Then, a light beam illuminates target phototransistor-controlled electrodes to increase local photocurrents to temporally deactivate that negative DEP trap as shown in FIG. 1(*c*). Finally, the target particle(s) or cell(s) can be released from their lock site(s) and transported away by fluid flows for downstream collection and analysis as shown in FIG. 1(*d*). Alternatively the target particle(s) or cell(s) can be retained for further examination and/or manipulation.

Figure 2:
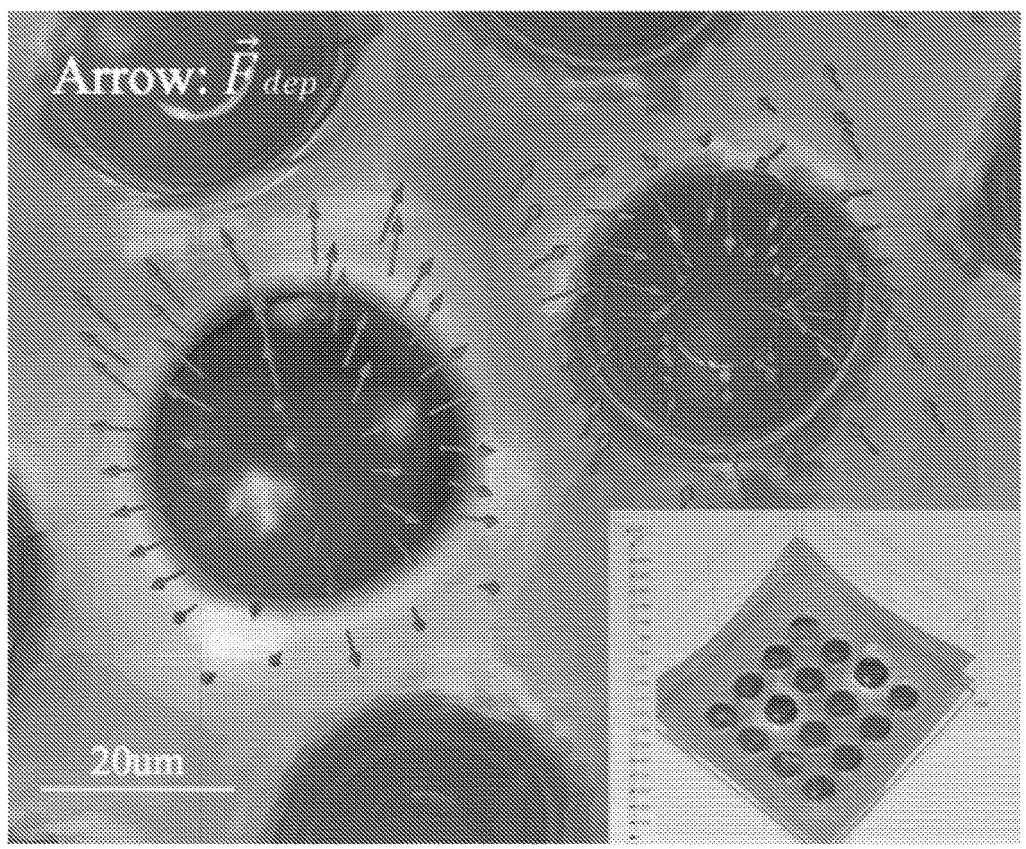
FIG. 2 shows a simulation demonstrating the operating principle of SLOT by plotting the iso-surface of the square of the electric field and the direction of DEP forces at ring electrodes with and without light illumination.

Computer simulation was used to verify the concept during the design process. COMSOL was used to simulate the operating principle of SLOT as shown in FIG. 2. A negative DEP trap was formed at the annular phototransistor if an AC voltage is applied. The AC frequency was chosen such that part of the applied voltage can leak through the SU-8 insulator at the large electrode area. This is how particles or cells can be locked in ring phototransistors in the dark state. When a light beam illuminates the phototransistor connecting the large electrode with a floating island electrode, it turns on the floating electrode to create a stronger electric field in the island electrode region than the large electrode area covered by the insulator. This repels the locked particle away by negative DEP force.

Figure 14:
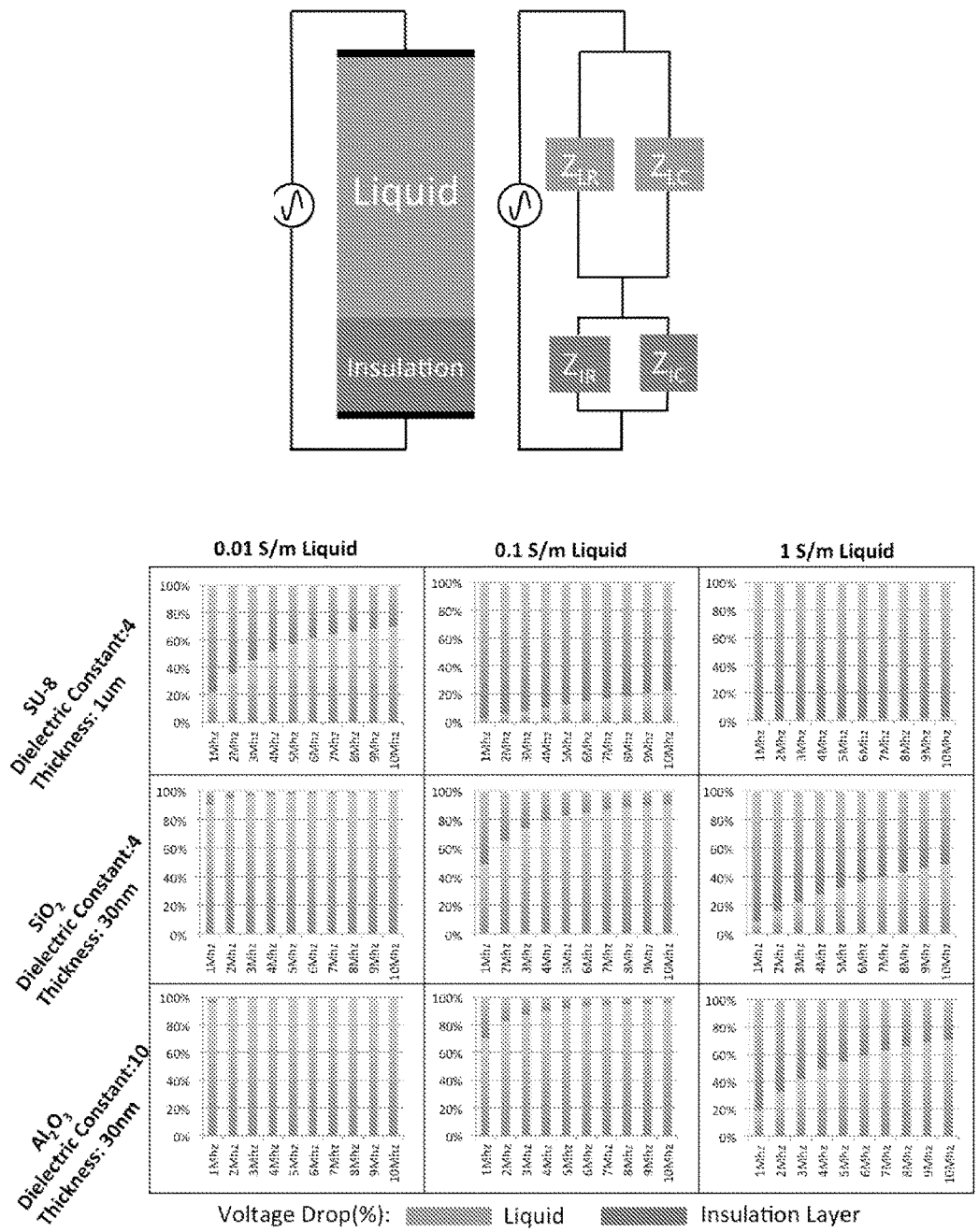
FIG. 14 shows a comparison of the effects of different insulation layers on SLOT operation. The partial voltage leak is calculated for nine different combinations of insulation layers and liquid conductivities. Based on the calculation we conclude that 30 nm $Al_2O_3$ should outperform the other two insulation layers within 1 S/m high conductive media in terms of achieving self-locking and releasing function at the same time.

As noted above, the self-locking function in SLOT can be realized by the partial voltage leak in the background in the dark state. This leak voltage is dependent upon several parameters including the thickness of the insulation layer, its dielectric constant, the operation AC frequency, and the medium conductivity. To understand these relationships, a simple lump element model was utilized to calculate the ratio of voltage drop across the liquid layer and the insulation layer under nine different conditions. In an ideal SLOT operation condition, the insulation layer should allow a roughly 50% partial voltage leak such that strong enough self-locking forces can be provided in the dark state, while maintaining sufficient electric field strength gradient to be created to repel the trapped cell out in the bright state. FIG. 14 presents calculated results of leak voltage drop in the dark state for insulation layers of 1 μm SU-8, 30 nm $SiO_2$ and 30 nm $Al_2O_3$ with each of them in media with electrical conductivity of 0.01 S/m, 0.1 S/m and 1 S/m. In one extreme case of using a thick dielectric layer in a highly conductive medium (1 μm SU-8+1 S/m), there is no self-locking function since most voltage drop across the insulation layer. In another extreme case of using a high k and thin dielectric in a less conductive medium (30 nm $Al_2O_3$+0.01 S/m), self-locking function is strong in the dark stage but no releasing function is allowed in the bright state since the nearly 100% leak voltage drop in the medium eliminates the room for creating electric field strength gradient in the bright state required for repelling the trapped cell. Therefore, the optimization of the insulation layer thickness and materials and matching with operation media is important for SLOT operation and a high k dielectric (e.g., 30 nm $Al_2O_3$) is particularly well suited for operation in a conductive solution (e.g., a physiological buffer solution).

The composition and thickness of the insulation (dielectric layer) can be precisely controlled during fabrication. For example, the high k dielectric can readily be precisely deposited using atomic layer deposition (ALD) methods.

Figure 3A:
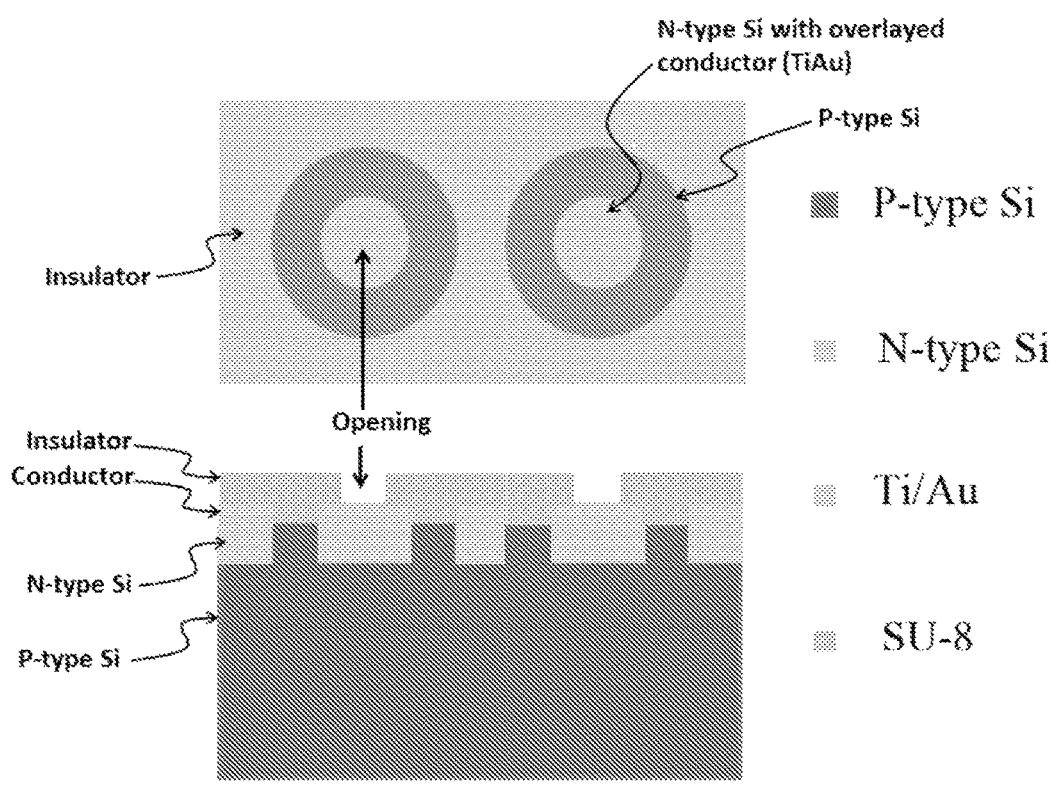
FIGS. 3A and 3B show a top view and side view of one illustrative SLOT platform.
Figure 3B:
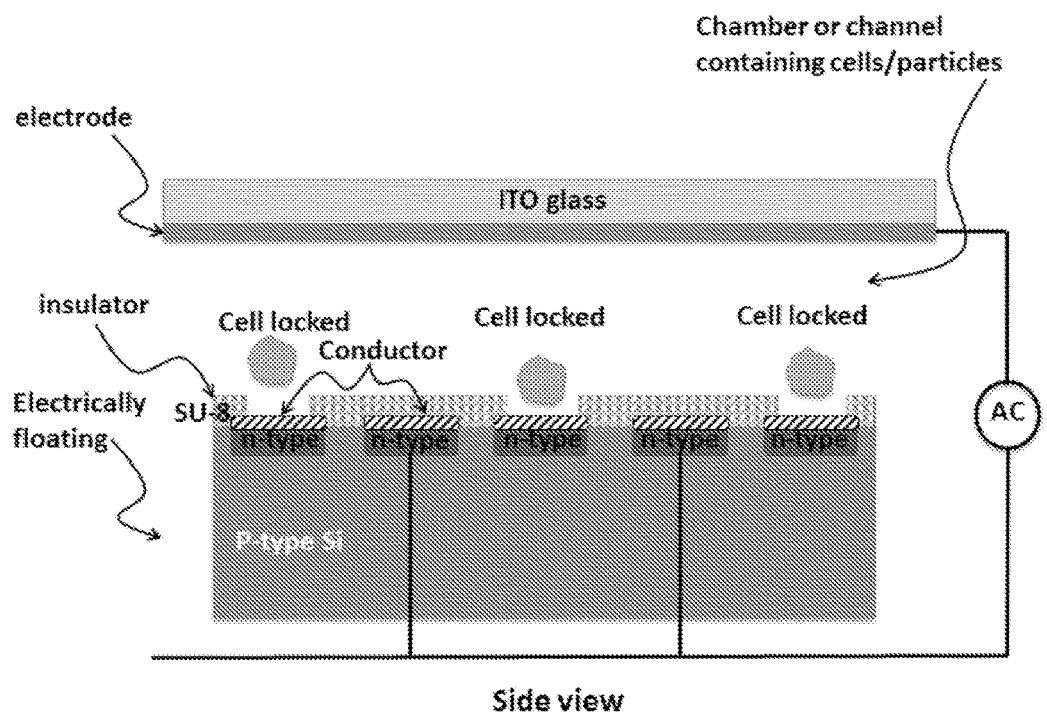
Figure 3B:
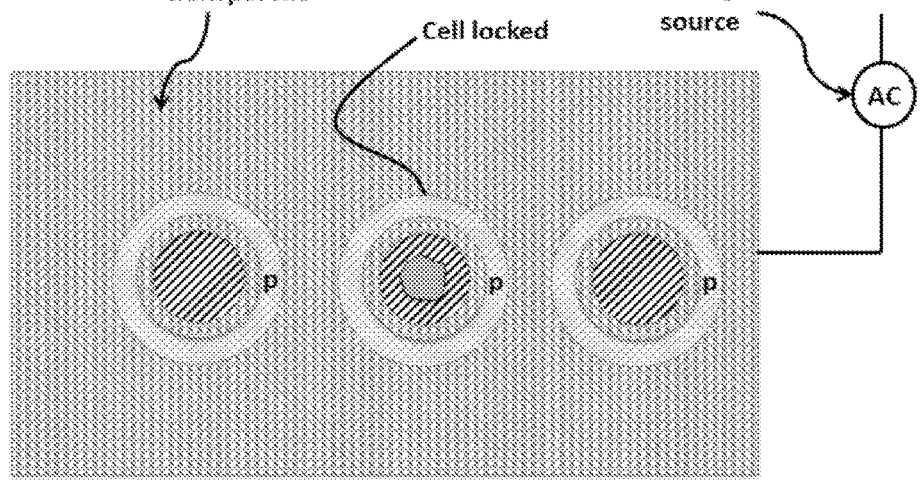
Figure 9:
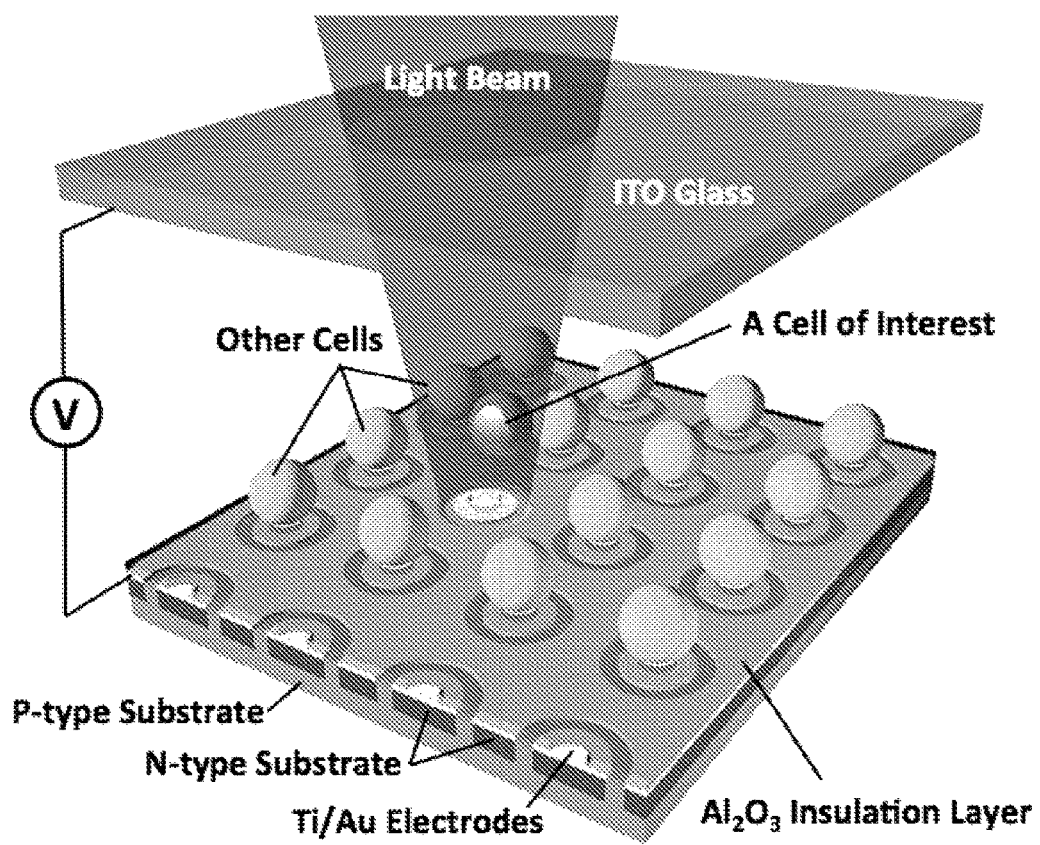
FIG. 9 schematically illustrates one embodiment of a Self-Locking Optoelectronic Tweezers (SLOT) platform. The platform utilizes an array of ring-shaped, lateral phototransistors as optical sensors to trigger DEP forces. A high k dielectric layer (e.g., 30 nm $Al_2O_3$) is coated to ensure partial voltage leak in the dark state to realize the single cell self-locking function. Optical illumination turns off the locking function and releases the illuminated cell.

FIGS. 3A and 3B illustrate the top-view and side-view of certain embodiments of a SLOT platform. The illustrated device is fabricated on a p-type silicon substrate. Ring-shape patterns electrodes were formed by photolithography. Between the large electrode and the island electrodes, n-type ion implantation was done to create npn phototransistors. A 100 nm gold (Au) on 10 nm titanium (Ti) thin film was patterned in the p-type regions on the substrate for electrical contacts. N-type substrate with p-type ion implantation can also be fabricated to create pnp type phototransistors to control the floating island electrodes. The photodetector structure is not limited to phototransistor. Other structures such as photoconductor and metal-semiconductor-metal (MSM) can also work in principle. A final SU-8 patterning was used to create openings in the floating island electrode regions for fluid contact. Other dielectric materials such as PDMS, silicon dioxide, $Al_2O_3$, silicon nitride or others can also be used to replace SU-8 for partial electrical insulation. Architecture of another SLOT platform is illustrated in FIG. 9.

The prototype of SLOT has been successfully fabricated and tested. In a proof-of-concept device, we performed experiments with microparticles (10 μm in diameter) and cells suspended in regular physiological buffers, or in isotonic buffers with a conductivity of 0.1 S/m. In principle, SLOT also functions in other aqueous media with conductivities varying from DI water to 5 S/m with properly designed device parameters.

Figure 4:
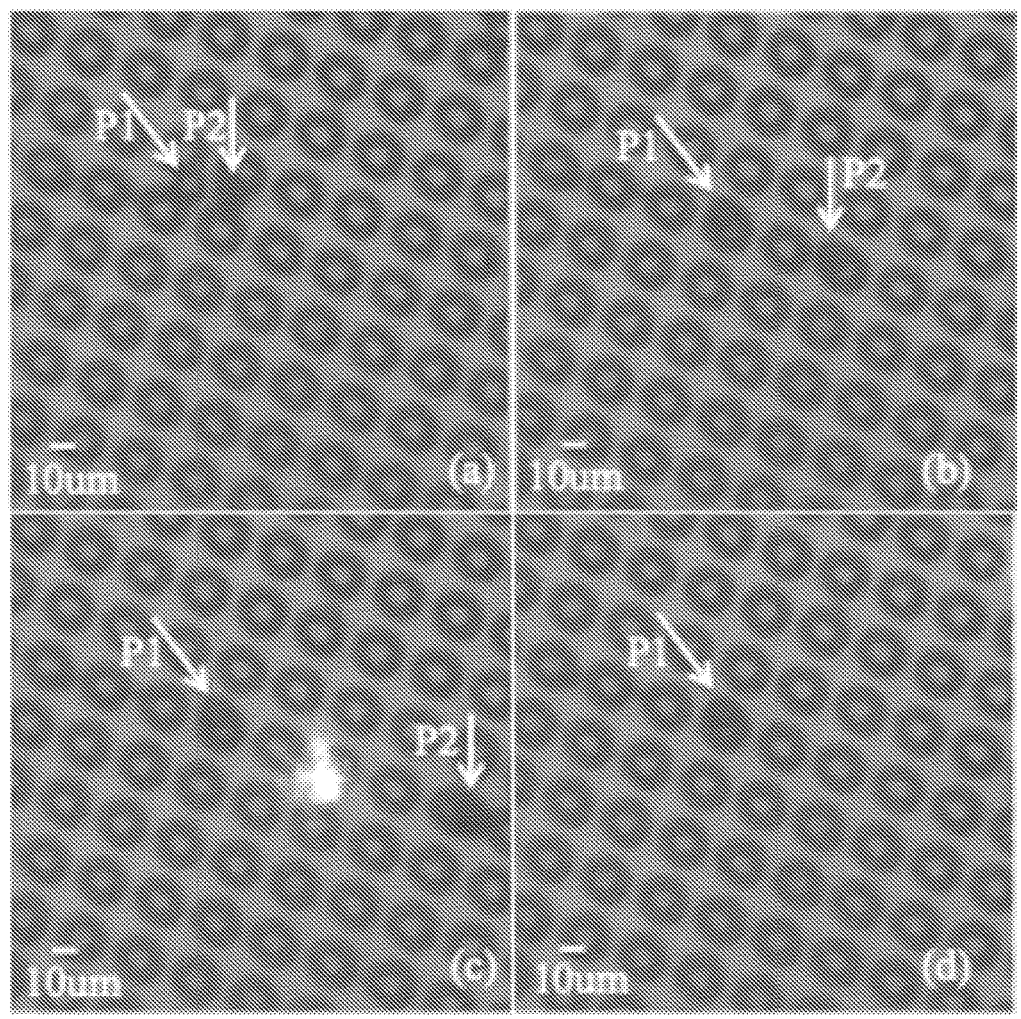
FIG. 4, panel (a) Voltage-off and Light-off. Two particles are flowed in through a microfluidic channel.

FIG. 4 demonstrates the self-locking and selective releasing functions of SLOT.

A unique feature of SLOT is the self-locking function in the dark state. When a group of particles or cells are introduced onto a SLOT platform, they are individually locked in ring-shaped (annular) phototransistor-controlled electrodes by negative DEP forces without light beam illumination. When a light beam illuminates one or more annular phototransistors, it turns off the DEP trap in those phototransistors to release the trapped microparticle or cell. Since the particles or cells are self-locked in the dark state, a large number of ring-phototransistors and associated electrodes can be deployed across a large area (e.g., across tens of even hundreds of $cm^2$) to trap millions of particles or cells without active light beams.

An optical illumination system with a limited field of view (FOV) but high optical resolution can scan across the entire wafer to selectively release trapped cells or particles sequentially, similar to a stepper concept used in modem photolithography. Alternatively certain areas can be illuminated (e.g., using a mask) to release a number of cells or particles in selected regions of the substrate. As a consequence, the operation area of SLOT is not limited by the FOV of objective lenses for imaging and optical pattern projection. For comparison, in regular OET operation, the microparticles in the regions without light illumination will be rinsed away by fluid flows.

Moreover by coupling the illumination system with a detection system, particular cells or particles (e.g., cells or particles having a particular color or morphology, or labeled with particular, e.g., fluorescent labels) can be selectively released or selectively retained. In this manner, the SLOT systems described herein can function as effective sorters (e.g., cell sorters).

Figure 15:
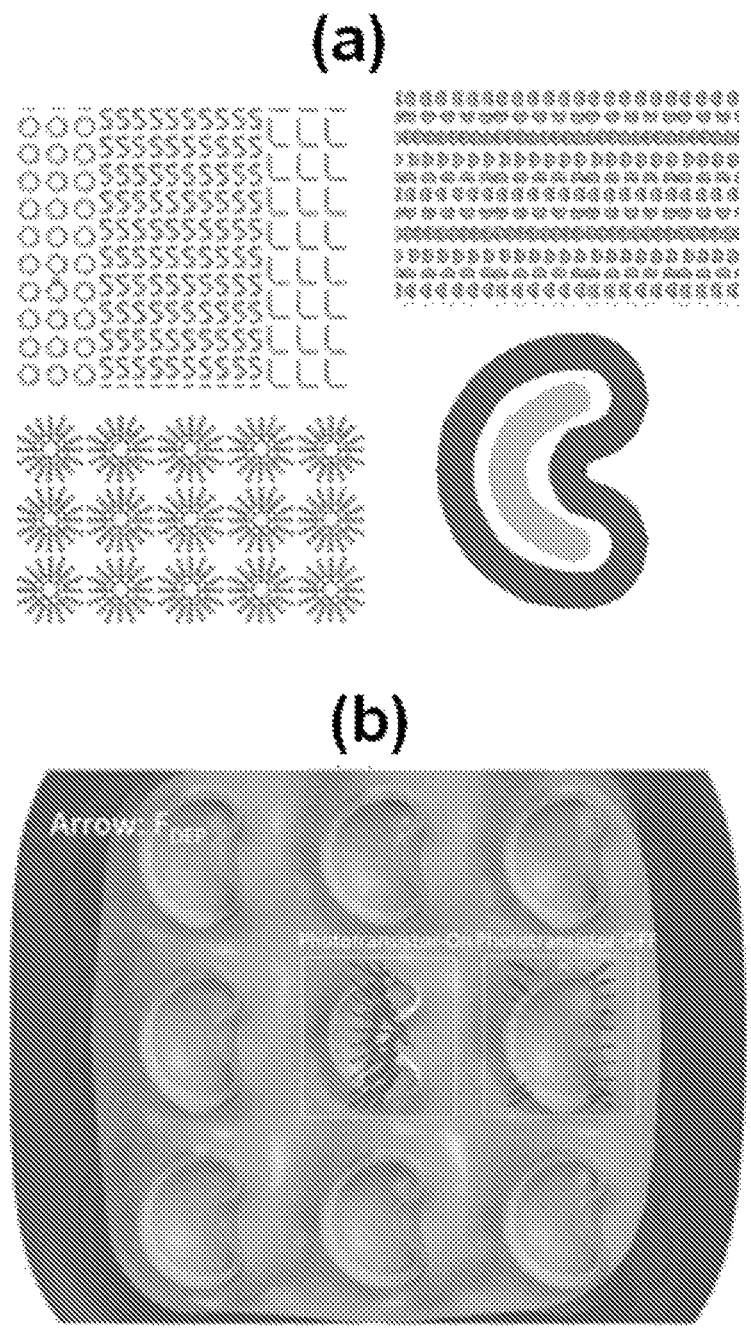
FIG. 15, panels (a)-(c), illustrates non-circular phototransistors of SLOT. Panel (a): The fabrication process is the same as SLOT. In one embodiment of a non-circular SLOT, however, the P region (blue region) has been designed to be "bean" shaped (e.g., kidney bean shaped) instead of circular. The green region represents opening area on high k dielectric coatings for electrode-liquid contact. Panel (b): Simulation of Non-circular SLOT. Panel (c): Particle migration along a circle step by step (2 Mhz,0.1 S/m,5Vpp).

While the SLOT described above with respect to annular (circular) phototransistors, the phototransistors need not be limited to this shape. In various embodiments, non-circular phototransistors are contemplated. Such phototransistors can include, inter alia other regular polygons, oval phototransistors and irregular phototransistors including, but not limited to kidney-shaped phototransistors. Using circular phototransistor configurations, cells or microparticles will only experience symmetric DEP force, which means the releasing direction will exclusively depend on the direction of the background flow. The non-circular phototransistor design (see, e.g., kidney shape in FIG. 15) can be used to generate asymmetric electrical field, resulting in a directional DEP force. The advantage of non-circular design is that the system can operate even without external fluidic pumping system. Using individual non-circular phototransistors as building blocks, the combination of large number of electrodes can be very powerful. For example, we have shown that with a well-controlled laser beam single particles can migrate along with arbitrary pre-designed path (straight line, loop, etc.).

The fabrication of non-circular phototransistors is the same as annular phototransistors in SLOT. The difference is in the design process where the shape of p region will be non-circular while the width of p region stays the same.

Example 1

Self-locking Optoelctronic Tweezers for Mircoparticle Manipulation Across a Large Area This example describes the design and fabrication of a novel Self-Locking Optoelectronic Tweezers (SLOT) platform that overcomes the blur optical pattern issue for large area single cell and microparticle manipulation. SLOT is realized by laying out an array of ring shaped (annular) phototransistors that can be optically turned on and off. Single cells and microparticles are self-locked into these annular phototransistors in the dark state without light illumination. When a light beam illuminates a ring-shape electrode, it turns off the DEP trap in that electrode to release the trapped microparticle. Since cell and microparticles are self-locked in the dark state, a large number of annular phototransistors can be deployed across a large area across tens or even hundreds of cm$^2$ to trap millions of single cells. An optical illumination system with a limited field-of-view (FOV) can scan across to selectively release trapped cells across the entire wafer, similar to a stepper concept used in modern photolithography. As a consequence, the operation area of SLOT is not confined to the FOV of objective lenses for imaging and optical pattern projection. In addition, SLOT is also a single crystal silicon phototransistor-based platform. It provides the potential for single cell manipulation in regular physiological buffers (Hsu et al. (2010) *Lab Chip*, 10(2): 165-172).

Device Operation and Principle.

FIG. 1 schematically illustrates operation of one embodiment of a SLOT platform illustrative configurations of which are shown in FIGS. 3A and 3B. As illustrated the SLOT system comprises a top surface comprising an electrode, bottom phototransistors and fluid channels or chambers (e.g., microfluidic channels) in between. Particles or cells are introduced onto the platform, e.g., flowed in through a microfluidic channel.

The top and bottom electrodes (see, e.g., FIG. 3B) are electrically connected to a voltage source (e.g., a function generator). Once a voltage (e.g., an AC voltage) is applied to the electrodes, DEP traps are formed and lock individual particles (or cells) to their neighboring phototransistor ring electrodes. Next, optical observation (e.g., fluorescence, dark field, phase contrast, and others), or other observation, can be performed to identify particles or cells of interest. Then, a light beam illuminates target phototransistors which increases local photoconductivity, and temporarily de-activates the respective DEP trap. Finally, the target single particle or cell (or a cluster of particles or a cell cluster) is released from the locking site and transported away, e.g., by a continuous flow for downstream collection and analysis. Alternatively target particles or cells (or particle clusters or cell clusters) can be retained for analysis or further processing and undesired particles or cells (or particle clusters or cell clusters) can be released.

In certain embodiments, the light beam can be directed to individual phototransistor sites to release the moieties captured in a single DEP trap. In certain embodiments, the light beam can be directed to a plurality of phototransistor sites, e.g., using a mask to release moieties captured at multiple DEP traps.

Device Fabrication and Simulation

FIGS. 3A and 3B illustrate a top-view and side-view of an illustrative SLOT platform. The illustrated device is fabricated on a p-type silicon substrate (e.g., on a highly doped p-type substrate). Ring-shape patterns are formed by photolithography and then used as a mask for n-type ion implantation. A 100 nm gold (Au) on 10 nm titanium (Ti) thin film is then evaporated onto the substrate followed by SU-8 patterning to create openings for electrode contact with fluid. We used COMSOL to simulate the operating principle of SLOT as shown in FIG. 2. A negative DEP trap is formed at the ring electrode if only an AC voltage is applied. The AC frequency is chosen such that part of the applied voltage leak through the SU-8 insulator at the large electrode area. When a light beam illuminates the phototransistor connecting the large electrode with the floating island electrodes, it turns on the floating electrode to create a strong electric field in the island electrode that repels the trapped particle away by negative DEP forces.

It will be recognized that the configurations shown are illustrative non-limiting. It will be recognized, for example that the device can be configured with the doping reversed to form annular n-p-n phototransistors. Additionally, the dimensions can be varied, e.g., as described and claimed herein.

In one proof-of-concept device, we performed an experiment with microparticles (10 μm in diameter) suspended in an isotonic buffer with an electrical conductivity of 0.1 S/m. In FIG. 4, we demonstrate self-locking and selective releasing of single particles on SLOT. SLOT can be scaled up to enable operation over a large area.

The data presented herein demonstrate a novel SLOT platform for self-locking and selective releasing of single microparticles and single cells (or clusters of microparticle and cell clusters) across a large area. In one illustrative embodiment, SLOT is a single crystalline phototransistor based OET system that has the potential for single cell manipulation in regular physiological buffers. However, SLOT does not necessarily need to be fabricated on single crystalline silicon. SLOT's particle manipulation concept can be realized on amorphous or polysilicon based annual phototransistor structures. Other semiconductor materials such as Group III-V materials can also be used.

Operational Parameters of an Illustrative, but non-limiting Embodiment

Figure 5:
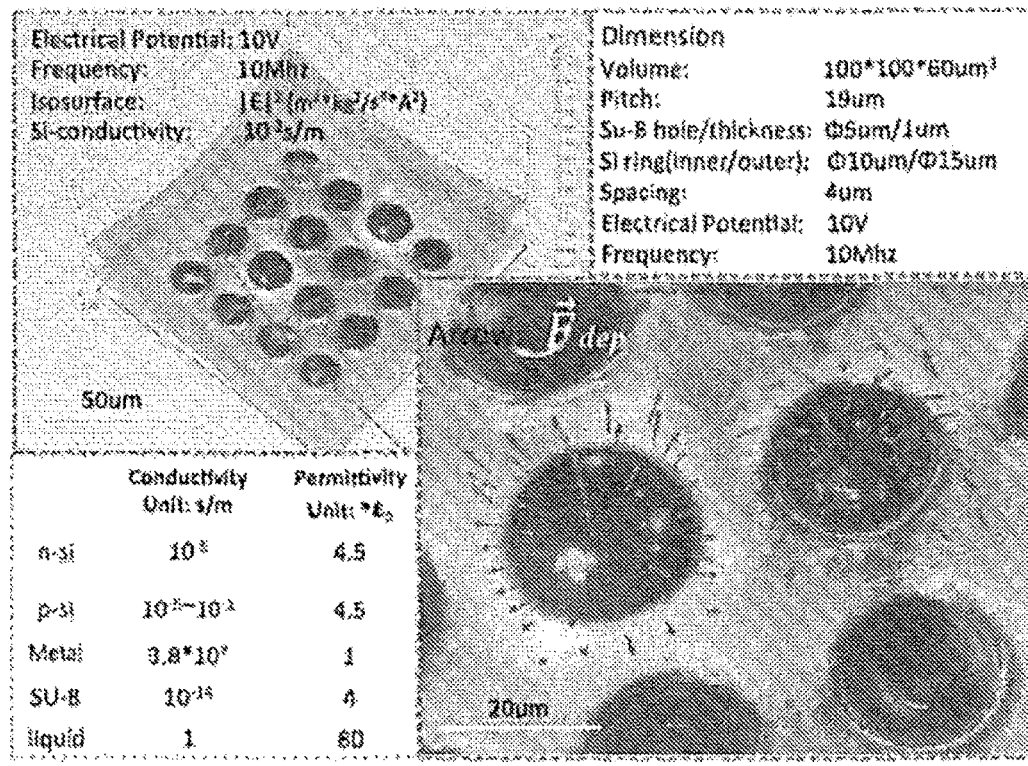
FIG. 5 illustrates operating parameters for one illustrative embodiment of SLOT. Simulation of self-locking and releasing effect.
Figure 6:
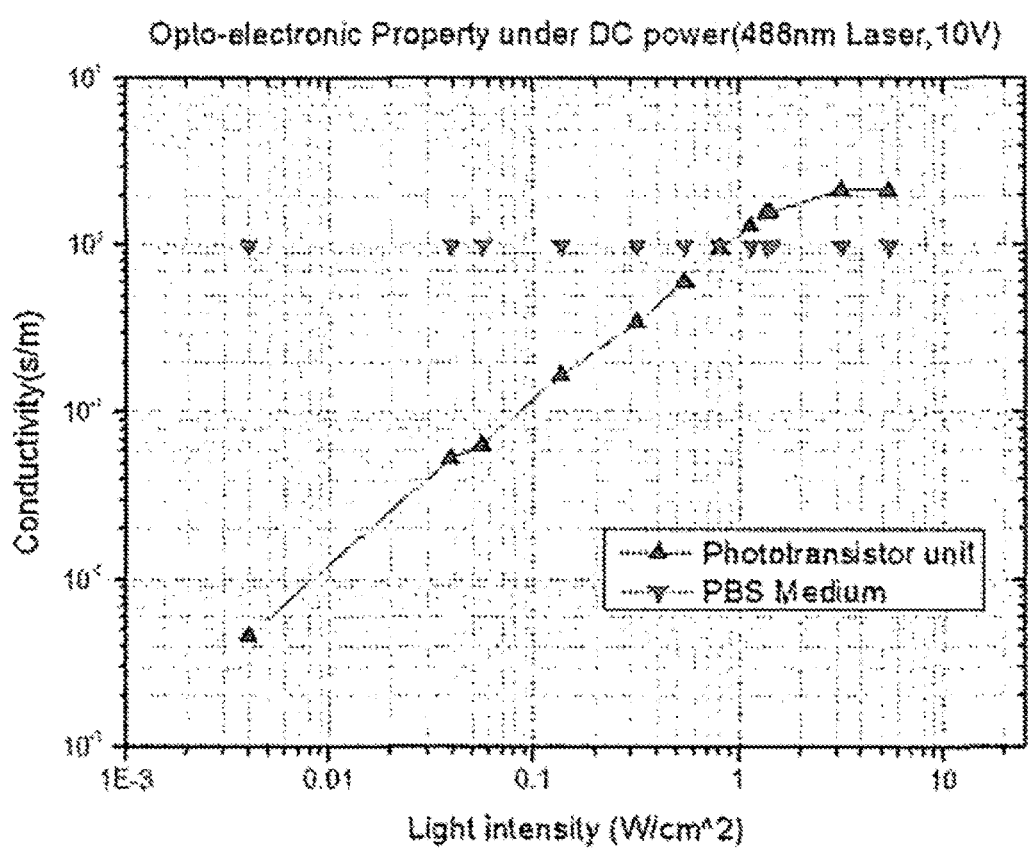
FIG. 6 illustrates opto-electronic properties of one embodiment under DC power (488 nm Laser, 10V).
Figure 7:
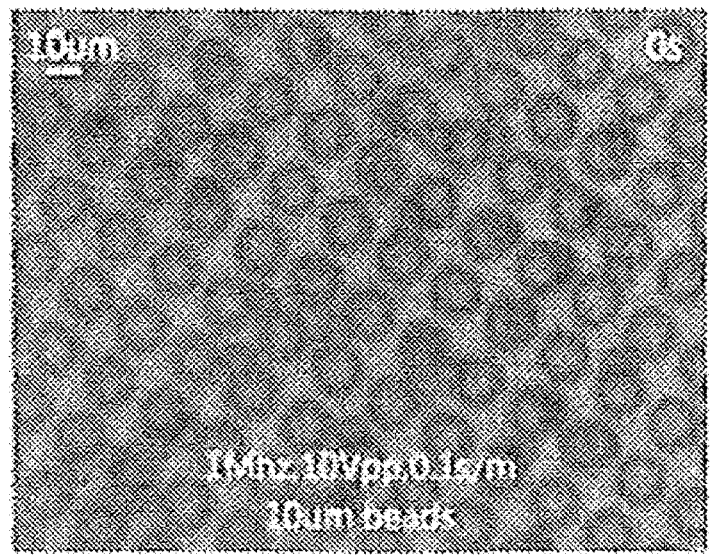
FIG. 7 illustrates a test of the self-locking process.
Figure 7:
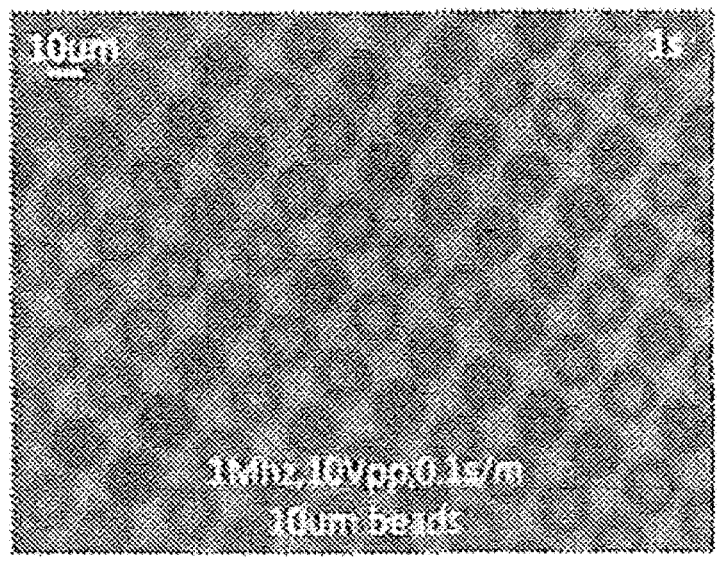
Figure 8:
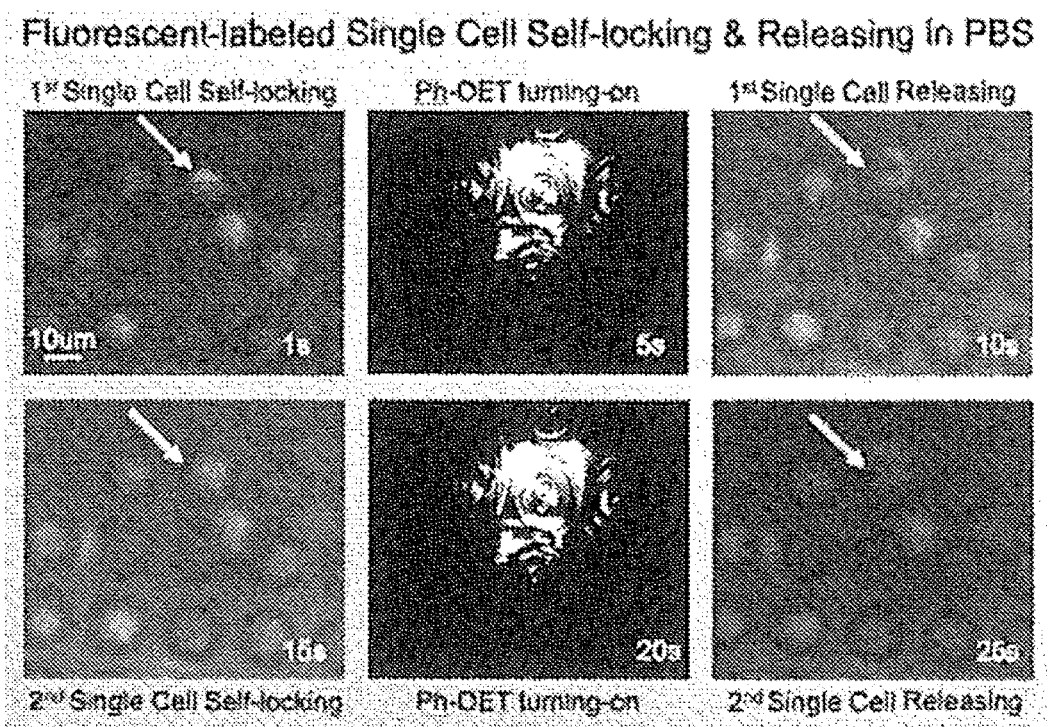
FIG. 8 illustrates single cell locking and releasing of a fluorescent labeled cell in PBS.

Fabrication of a high sensitivity SLOT:
Junction width: 2 μm;
Ion implantation: 1e15 cm$^{-2}$ 200 keV, 4e15 cm$^{-2}$ 15 keV (surface);
Annealing: 1000° C., 1 hour
Electrode: Au(100 nm) on Ti (10 nm)
Insulation layer: 2 μm.
Simulation of elf-locking and releasing (see, e.g., FIG. 5);
Automatic single cell trapping over a large area;
Selectively single cell releasing over a large area; Vpp (voltage), 10 MHz (frequency), 20 μm (device pitch), 1 S/m (medium conductivity).
Opto-electronic property test (see, e.g., FIG. 6).
1000 times photoconductivity increase under DC power;
Conductivity: off-state (0.005 S/m)<<PBS medium (1 S/m)<on-state (2 S/m);
Test of large area self-locking effect (see, e.g., FIG. 7).
10 Vpp (voltage), 10 MHz (frequency), 20 μm (device pitch), 1 S/m (medium conductivity)
Single cell self-locking & releasing within regular PBS buffer (see, e.g., FIG. 8)
Single cell self-locking effect observed;
Selectively fluorescence-labeled single cell releasing observed;
10 Vpp (voltage), 10 MHz (frequency), 20 μm (device pitch), 1 S/m (medium conductivity, PBS).

The foregoing embodiments are intended to be illustrative and non-limiting. Variations will be recognized by one of skill in the art. For example, the size of the annular regions comprising the device can depend on the application. For trapping of cells (or particles) of size ~10 µm the annulus of about 15 µm in diameter, as illustrated herein is suitable. For trapping larger cells, cell clusters, other collections of cells, eggs, and the like larger size annuli will suffice. To trap smaller particles or bacteria (e.g., about 1-2 µm) small size annuli will suffice. Accordingly in certain embodiments the annulus diameters ranging from about 1 µm, or from about 2 µm, or from about 5 µm, or from about 10 µm, or from about 15 µm up to about 200 µm, or up to about 150 µm, or up to about 100 µm, or up to about 50 µm, or up to about 40 µm, or up to about 30 µm are contemplated. In certain embodiments, the annuli range from about 5 µm to about 50 µm in diameter.

The width of the doped ring forming the annular transistor will control the transistor properties. In certain embodiments annulus thicknesses range from about 0.5 µm up to about 10 µm. Thinner annulus rings can provide a higher photo gain that allows the use of lower light intensities to turn on the electrode. But the trade-off is the small voltage amplitude it can operate since the phototransistor can be turned on under high voltage without light illumination. If a larger width is used the photo gain could be lower, but on the other hand, we can operate the device in high voltage to generate larger trapping forces on cells.

Example 2

Single Cell Manipulation in Cell Culture Media With Self-Locking Optoelectronic Tweezers Across a Large Area This example describes a novel Self-Locking Optoelectronic Tweezers (SLOT) for single-cell manipulation in cell culture media across a large area (see, e.g., FIG. 9). SLOT overcomes two major technical barriers of conventional optoelectronic tweezers (OET) toward high throughput single-cell manipulation. In one illustrative, but non-limiting embodiment, SLOT is fabricated by laying out an array of lateral phototransistor based, ring-shaped electrodes that can be optically turned on and off. The lateral, ring-shaped phototransistor design enables manipulation in high conductivity media (1 S/m) and overcomes a fundamental blurry optical pattern issue for single-cell manipulation in large area (>1 cm$^2$).

Principle of Operation.

DEP traps, powered by an external function generator, are formed around ring-shaped electrodes where single cells are self-locked in the dark state without light illumination. When a light beam illuminates a ring electrode, the DEP trap is turned off to release the illuminated single cell. This operation mechanism can be easily scaled up to an ultra large area, even across a whole wafer to trap millions of single cells in parallel. The operation concept of SLOT is similar to a stepper used in modern microfabrication. Optical illumination system can scan across the whole wafer to release cells of interest while the other out-of-FOV cells remain self-locked.

Simulation and Fabrication

Figure 10:
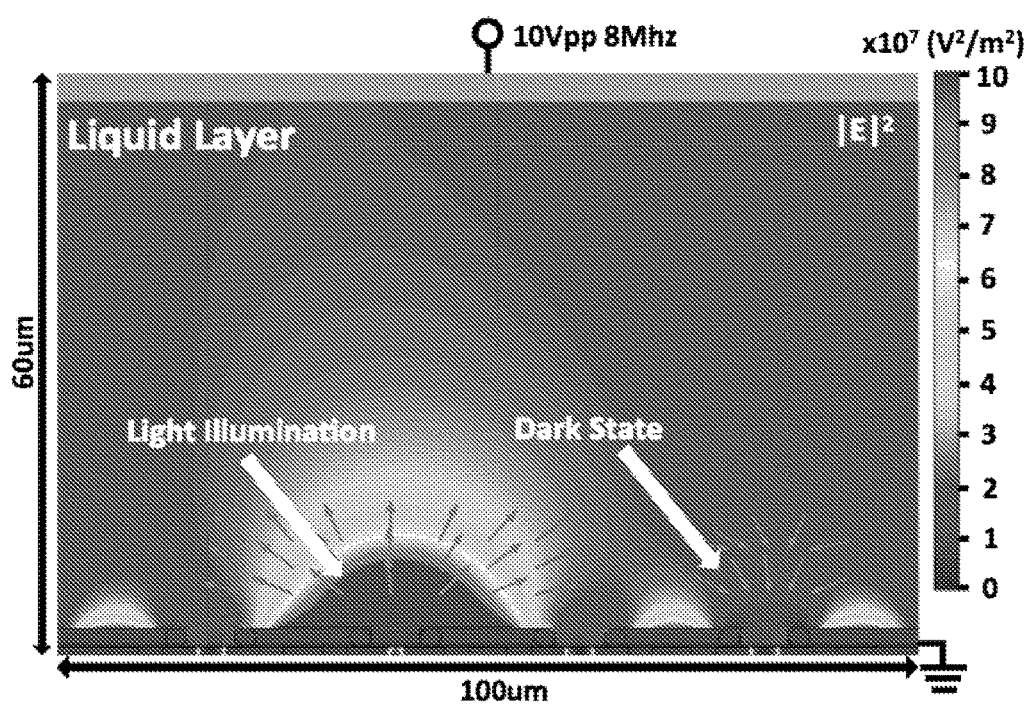
FIG. 10 illustrates the results of a numerical simulation showing the electric field distribution and DEP force directions (arrows) at a light-illuminated pixel and a dark pixel on a SLOT platform. In the dark state, negative DEP forces will lock a cell to the electrode center. In the bright state, a locked cell is pushed out of the electrode center.

SLOT has two operation states: dark state and bright state. In a dark state, only ac voltage is applied. In a bright state, both ac voltage and illumination light beam are applied. To understand how SLOT works under a dark state and a bright state, it is useful to conduct numerical simulations. FIG. 10 shows the numerically simulated electric field intensity distribution and DEP forces at a light illuminated pixel and a surrounding dark pixel. A high frequency (10 MHz) ac bias is applied to create partial voltage leak through the $Al_2O_3$ insulation layer (30 nm) to form negative DEP single cell traps in the dark state. The DEP force points to the electrode center in a dark state, locking single cells. Conversely, in a bright state, the DEP force points out of the electrode center thereby releasing single cells. This is the fundamental reason why self-locking and selective releasing can be achieved. The decoupling of self-locking and light releasing function promises the extension of SLOT to an ultra large area.

In one illustrative embodiment, the device is fabricated on a p-type highly doped single crystalline silicon substrate. Ring-shaped patterns are generated from photolithography and serve as an n-type ion implantation mask. A 100 nm (Au) on 10 nm (Ti) metal thin film is evaporated to the substrate followed by a lift-off process. Finally, we pattern a 30 nm $Al_2O_3$ thin film with an array of 5 µm circular openings for electrode-buffer contact. It is worth noting that the choice of $Al_2O_3$ thin film is due to the important role it plays in achieving both self-locking and releasing functions. The film should be thin and with high dielectric constant such that the electrical field from ac voltage can partially leak through the thin film in the dark state to enable the self-locking function. Biocompatible double-side tapes are patterned by a commercial paper cutter and serve as a microfluidic channel through which cell samples can be introduced. The channel width is roughly 200 µm. Unlike traditional vertical phototransistor design, we have proposed and realized a lateral phototransistor design that requires only one-time ion implantation and no trench isolation. The doping concentration and thickness of ion implantation has been optimized. The biggest advantage of a lateral design, compared to a vertical design, is that DEP trapping no longer relies on light illumination such that the trapping area can be extended to a whole-wafer level. Another benefit of lateral design is that the photon and electron path are separated so that we have the freedom to tune the light absorption and device structure independently.

Device Characterization

We further integrate a laser scanning system with fluorescent microscope to perform device characterization and calibration of operation conditions. A 532 nm 10 mW green laser is guided and focused onto the device surface through a set of labview-controlled scanning mirrors. A linear polarizer is used to adjust the laser power such that the light intensity is between 0.5 W/cm$^2$ and 5 W/cm$^2$.

Figure 11:
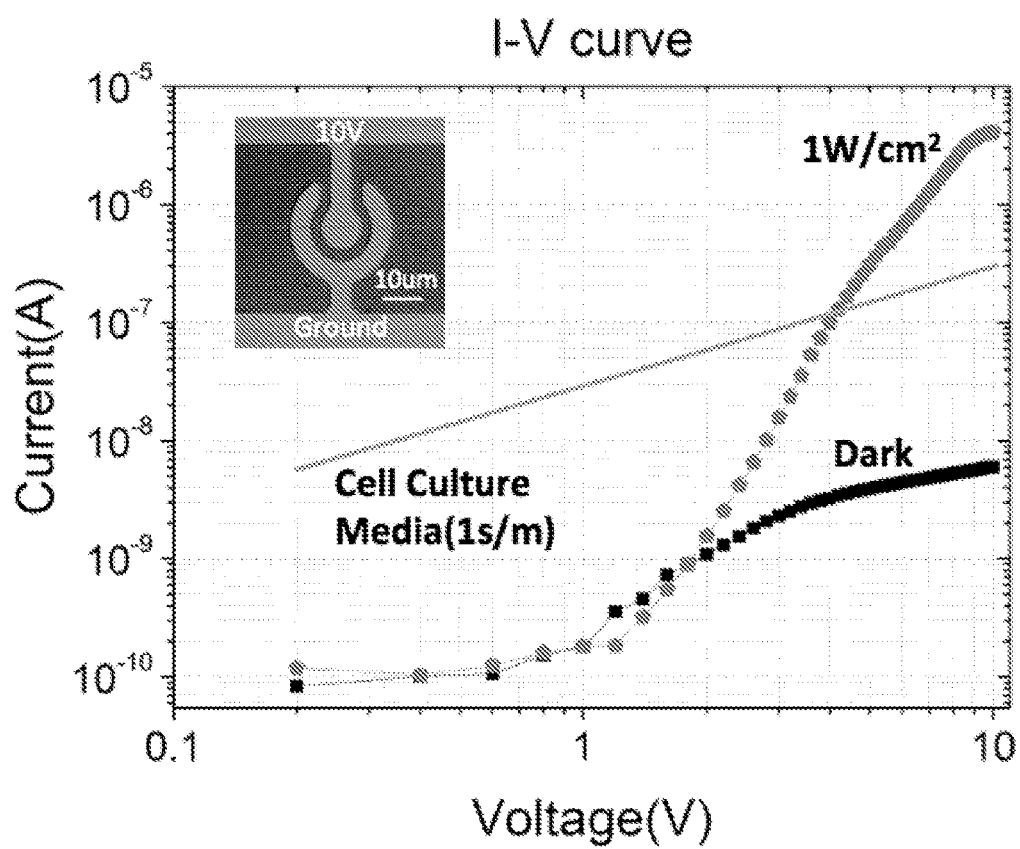
FIG. 11 illustrates the results of an I-V curve measurement showing the dark and photocurrent of a ring-shaped transistor on the SLOT platform. A three-order of magnitude photocurrent increase has been observed to realize operation in regular cell culture media (~1 S/m). The reference line in orange indicates the conductivity of cell culture media. It is 10 times lower and 10 time higher than bright and dark state, respectively.

A circular test structure fabricated along with the actual device was used for electrical characterization as shown in FIG. 11. The I-V curve was recorded at 1 W/cm$^2$ illumination intensity. Due to the high phototransistor gain and carrier mobility in single crystal silicon, a three-order of magnitude higher photocurrent was observed in the bright state than that in the dark state under a 10 V peak-to-peak voltage. A reference line (in orange) that indicates the conductivity of cell culture media is also plotted, showing that the resistance of the phototransistor in the dark state is at least 10 times larger than that of the cell culture media while the resistance of the phototransistor in the bright state is 10 times smaller.

Experimental Results

Figure 12:
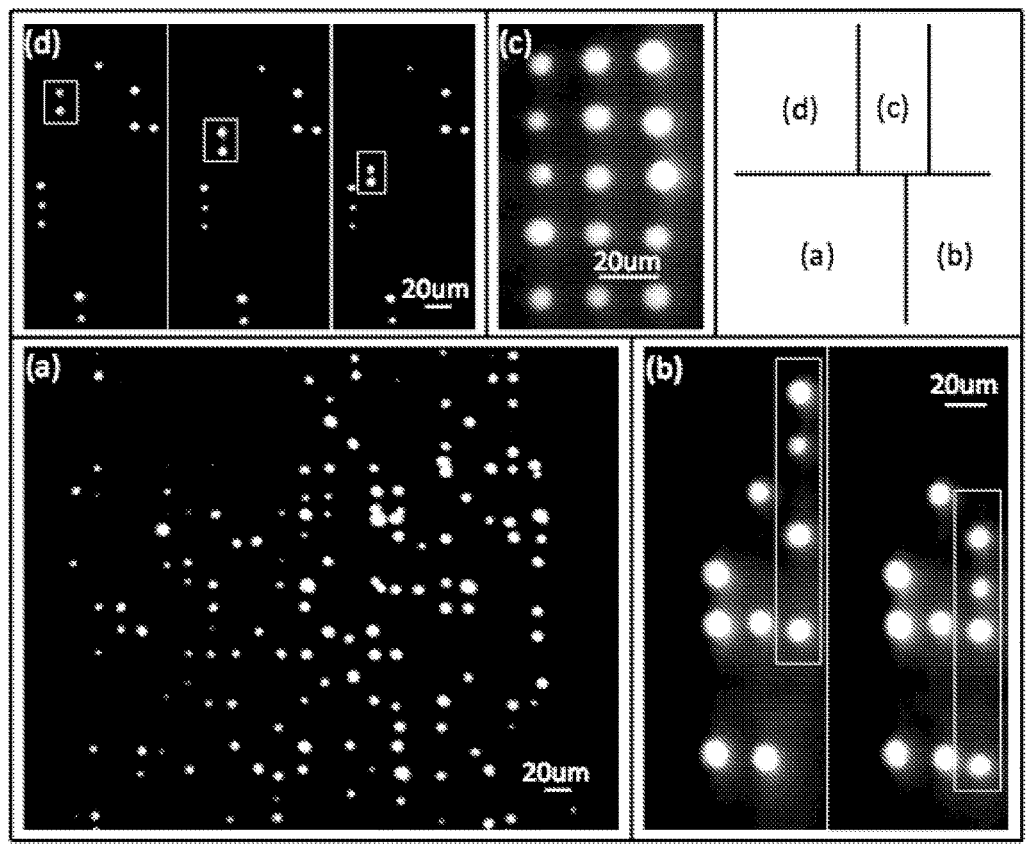
FIG. 12, panels (a)-(d), illustrates manipulation of 10 μm microparticles on a SLOT platform. Panel (a): Self-locking of microparticles across the whole FOV. Roughly 120,000 particles are self-locked across the 1 $cm^2$ chip. Panels (b) and (d): Individual manipulation of particles. Panel (c): Formation of a 5×3 particle array.

We demonstrate various manipulation functions of SLOT in cell culture media (DMEM) across an area of 1×1 cm$^2$ as shown in FIG. 12. Here we show large area self-locking, individual movement and array formation. In FIG. 12, panel a, self-locking across an ultra large area is demonstrated.

The total device working area is over 1 cm². However, we can only observe a relatively smaller area at a time simply due to the limitation of FOV of a microscope.

Based on the aforementioned discussion, the self-locking function is totally independent of observation such that as long as sufficient electrical power is provided, the effective self-locking area can be extended to even a whole-wafer level. In FIG. 12, panel b and FIG. 12, panel d, single cell manipulation is achieved through a projected laser beam. Multiple particles are released sequentially. In FIG. 12, panel c, a 5×3 array of microparticles is formed.

There are approximately 120,000 particles trapped over a 1 cm² SLOT platform and each of them can be sequentially investigated and optically released. One experimental detail that should be noted is that to enable ultra large area self-locking and releasing, a general purpose function generator alone may no longer be suitable since the power the device consumes could easily exceed the specifications, especially in a high conductive cell culture medium. Here we use a high power amplifier that is able to amplify 12 MHz ac inputs.

Single cell manipulation in regular cell culture media is critical for many real biomedical applications. However, most OET-based technology can only work in low conductivity media (typically ~0.01 S/m). Normal cell behaviors such as proliferation and growth cannot be expected in media other than regular physiological buffer (typically ~1 S/m). 5 µL of the sample solution (Ramos suspended in DMEM) is introduced to a SLOT device with an external function generator been set to 8 MHz and 10 Vpp. We show that a light beam within the field of view of the objective lens selectively releases a single cell of interest.

Figure 13:
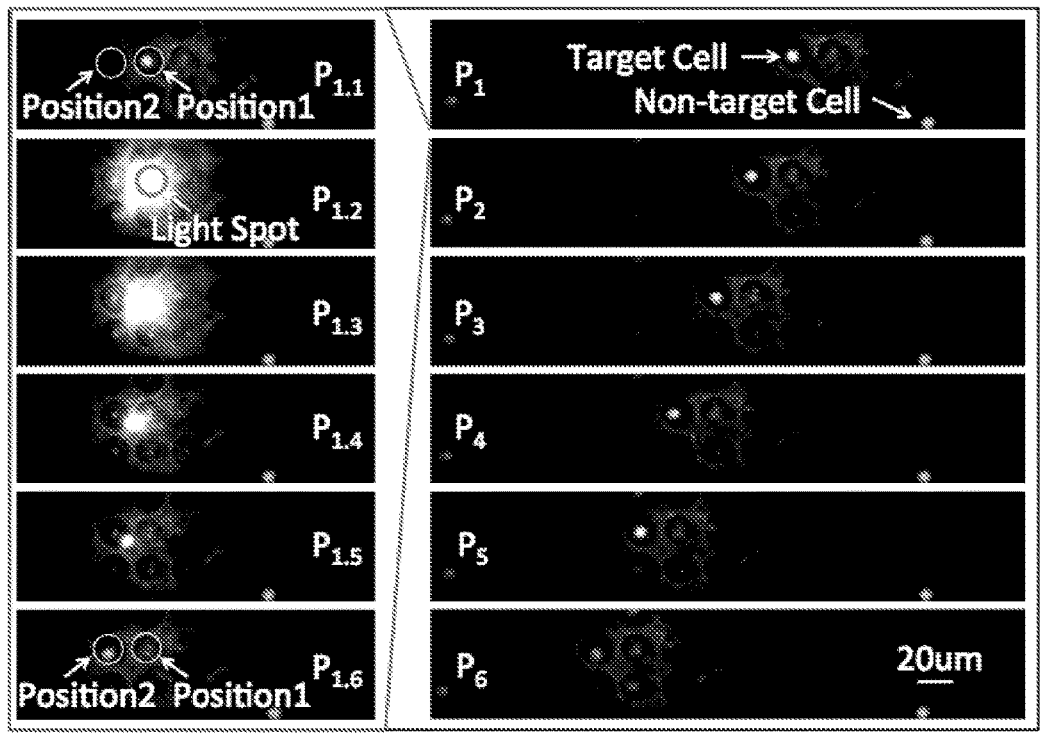
FIG. 13 illustrates single cell manipulation in a regular cell culture medium (DMEM) on a SLOT platform. Right: movement of a single target cell from position 1 to position 6. Left: details of moving a single target cell from position 1 to position 2.

In FIG. 13, we show how a target cell of interest was moved from position 1 to position 6 sequentially while a non-target cell remained locked. Originally, two cells were self-locked by the DEP traps. Then we moved the laser beam to where the target cell located. This resulted in a dramatic increase of photocurrent at the illuminated phototransistor. Thus, the DEP trap was turned off and the trapped cell was released by the background microfluidic flow. It takes less than 0.5 s to release a cell from a trap. The typical background flow speed was 50 µm/s. These parameters vary with different experimental conditions.

The operation of SLOT is similar to a "stepper" concept that is widely used in modern photolithography. We project fixed or programmable light pattern to a SLOT substrate. Cells of interest can be released one by one or batch by batch. Since the location of each electrode has been pre-designed, the releasing function can be performed without real-time observation, which indicates SLOT's capability to manipulate cells even beyond the field-of-view of the objective lens.

Conclusion

We report a novel Self-Locking Optoelectronic Tweezers (SLOT) for single cell manipulation in cell culture media across a large area. SLOT addresses two major technical barriers of conventional optoelectronic tweezers (OET) toward single cell manipulation in regular physiological buffers across a large area. Through its unique lateral, ring-shaped phototransistor design, high throughput (over 120,000 particles) manipulation in high conductivity media manipulation (>1 S/m) has been achieved. The self-locking concept is the key to extend the manipulation area of traditional OET to 1 cm², or even larger. Potential applications of SLOT include tissue engineering, drug screening (Nilsson et al. (2009) *Analytica Chimica Acta.* 649(2): 141457), cell-to-cell communication, rare cell sorting, and in vitro fertilization (Valley et al. (2010) PloS One. 5(4): e10160).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A self-locking optical tweezers device comprising:
   a first substrate comprising a plurality of ring-shaped phototransistors that can be optically turned on and off, wherein said first substrate is a doped p-type substrate where the center of the ring-shaped phototransistors and the regions outside said ring-shaped phototransistors are n-doped, and wherein said phototransistors and said first substrate are configured to produce a negative dielectrophoretic force (DEP) at the ring-shaped phototransistors on application of a voltage to said device; and that turn off the DEP at a ring-shaped phototransistor when that phototransistor is illuminated with light; and
   a surface comprising a second electrode, wherein said surface is disposed to define a chamber or channel between said first substrate and said surface and said chamber or channel is configured to receive and, or to hold a fluid containing cells or particles.

2. The device of claim 1, wherein said ring-shaped phototransistors are annular, or said ring-shaped phototransistors are bean-shaped.

3. The device of claim 1, wherein said phototransistors create an electric field perpendicular to the plane of the apparatus.

4. The device of claim 1, wherein said doped p-type substrate is doped p-type silicon.

5. The device of claim 1, wherein said n-doped regions are coated with a thin film conductor.

6. The device of claim 5, wherein said thin film conductor comprises one or more materials selected from the group consisting of Au, Ti, Al, Cr, Ni, Ta, Pd, and Pt.

7. The device of claim 1, wherein the diameter or the major axis of said ring-shaped transistors is about 10 nm to about 20 nm.

8. The device of claim 1, wherein:
   the thickness of the ring-shaped phototransistors ranges from about 0.5 µm up to about 10 µm; or
   the thickness of the ring-shaped phototransistors ranges from about 2 µm up to about 8 µm; or
   the thickness of the ring-shaped phototransistors is about 5 µm.

9. The device of claim 1, wherein said chamber or channel contains a physiological buffer.

10. The device of claim 1, wherein a top surface of said first substrate is coated with an insulator with openings to the centers of the ring-shaped phototransistors.

11. The device of claim 10, wherein said insulator comprises a material selected from the group consisting of SU-8 or other photoresists, PDMS, silicon dioxide, $Al_2O_3$, and silicon nitride.

12. The device of claim 11, wherein said insulation layer is configured to provide about a 50% partial voltage leak in the dark state.

13. A self-locking optical tweezers device comprising:
a first substrate comprising a plurality of ring-shaped phototransistors that can be optically turned on and off, wherein said first substrate is a doped n-type substrate where the center of the ring-shaped phototransistors and the regions outside said ring-shaped phototransistors are p-doped, and wherein said phototransistors and said first substrate are configured to produce a negative dielectrophoretic force (DEP) at the ring-shaped phototransistors on application of a voltage to said device; and that turn off the DEP at a ring-shaped phototransistor when that phototransistor is illuminated with light; and
a surface comprising a second electrode, wherein said surface is disposed to define a chamber or channel between said first substrate and said surface and said chamber or channel is configured to receive and, or to hold a fluid containing cells or particles.

14. The device of claim 13, wherein said ring-shaped phototransistors are annular, or said ring-shaped phototransistors are bean-shaped.

15. The device of claim 13, wherein said p-doped regions are coated with a thin film conductor.

16. The device of claim 15, wherein said thin film conductor comprises one or more materials selected from the group consisting of Au, Ti, Al, Cr, Ni, Ta, Pd, and Pt.

17. The device of claim 13, wherein the diameter or the major axis of said ring-shaped transistors is about 10 μm to about 20 μm.

18. The device of claim 13, wherein a top surface of said first substrate is coated with an insulator with openings to the centers of the ring-shaped phototransistors.

19. The device of claim 18, wherein said insulator comprises a material selected from the group consisting of SU-8 or other photoresists, PDMS, silicon dioxide, $Al_2O_3$, and silicon nitride.

20. The device of claim 19, wherein said insulation layer is configured to provide about a 50% partial voltage leak in the dark state.

21. A method of trapping cells or particles, said method comprising:
introducing cells or particles into a chamber of a device of claim 13; and
applying a voltage between said first electrode and said second electrode to trap said cells or particles at annular transistors comprising said substrate.

22. The method of claim 21, further comprising illuminating one or more phototransistors to release trapped particles or cells.

23. A self-locking optical tweezers device comprising:
a first substrate comprising a first electrode and a plurality of ring-shaped phototransistors that can be optically turned on and off, wherein a top surface of said first substrate is coated with an insulator with openings to the centers of the ring-shaped phototransistors, and wherein said phototransistors and said first substrate are configured to produce a negative dielectrophoretic force (DEP) at the ring-shaped phototransistors on application of a voltage to said device; and that turn off the DEP at a ring-shaped phototransistor when that phototransistor is illuminated with light; and
a surface comprising a second electrode, wherein said surface is disposed to define a chamber or channel between said first substrate and said surface and said chamber or channel is configured to receive and, or to hold a fluid containing cells or particles.

24. The device of claim 23, wherein said insulator comprises a material selected from the group consisting of SU-8 or other photoresists, PDMS, silicon dioxide, $Al_2O_3$, and silicon nitride.

25. The device of claim 23, wherein said insulation layer is configured to provide about a 50% partial voltage leak in the dark state.

26. The device of claim 17, wherein the diameter or the major axis of said ring-shaped transistors is about 10 μm to about 20 μm.

27. A method of trapping cells or particles, said method comprising:
introducing cells or particles into a chamber of a device of claim 23; and
applying a voltage between said first electrode and said second electrode to trap said cells or particles at annular transistors comprising said substrate.

28. The method of claim 27, further comprising illuminating one or more phototransistors to release trapped particles or cells.

29. A method of trapping cells or particles, said method comprising:
introducing cells or particles into a chamber of a device of claim 1; and
applying a voltage between said first electrode and said second electrode to trap said cells or particles at annular transistors comprising said substrate.

30. The method of claim 29, further comprising illuminating one or more phototransistors to release trapped particles or cells.

31. The method of claim 29, wherein:
said voltage is an AC voltage that ranges from about 0.5 V to about 100 V pp; and
the frequency of said voltage ranges from about 1 kHz to about 50 MHz.

32. The method of claim 29, wherein said chamber or channel contains a physiological buffer.

33. The method of claim 29, wherein said chamber or channel contains particles or particle clusters, or cells or cell clusters.

34. The method of claim 29, wherein:
said chamber or channel contains cells selected from the group consisting of prokaryotic cells, bacterial cells, eukaryotic cells, insect cells, mammalian cells, and avian cells.

* * * * *